US006214027B1

(12) United States Patent
Brossard

(10) Patent No.: US 6,214,027 B1
(45) Date of Patent: Apr. 10, 2001

(54) PREVENTION FACILITATOR SUPPORT FOR THE WRIST, ANKLE AND SACRO-LUMBAR JOINTS

(75) Inventor: André Brossard, Rosemère (CA)

(73) Assignee: Kirax International Inc., Montreal (CA)

( * ) Notice: Subject to any disclaimer, the term of this patent is extended or adjusted under 35 U.S.C. 154(b) by 0 days.

(21) Appl. No.: 09/347,192

(22) Filed: Jul. 2, 1999

(51) Int. Cl.[7] .............................. A61B 17/00; A61F 5/00; A61F 13/00

(52) U.S. Cl. .............................. 606/201; 602/19; 602/21; 602/27; 602/64; 602/65; 606/204

(58) Field of Search .................................... 606/201, 204; 128/96.1, 99.1, 100.1, 101.1; 601/134, 135

(56) References Cited

U.S. PATENT DOCUMENTS 4,243,028 * 1/1981 Puyana ................................ 606/204
5,470,304 * 11/1995 Decanto .............................. 601/134
5,769,810 * 6/1998 Brossard .............................. 602/65

* cited by examiner

*Primary Examiner*—Kim M. Lewis
(74) *Attorney, Agent, or Firm*—Birch, Stewart, Kolasch & Birch, LLP

(57) ABSTRACT

A device for controlling the reflex response of a muscle or muscular group articulating a living body joint by applying a specific mechanical stimulation (SMS) to the external area of the joint which corresponds to the mechano-receptors guiding a natural reflex of the muscle or muscular group. The embodiments of the device include a support member adapted to be mounted to the wrist ankle or lumbar spine joint, a pressure-applying member and a resilient portion interposed between the support member and the pressure-applying member to continuously apply a required pressure intensity during articulation movements of the joint. The mechano-receptors include skin mechano-receptors and deeper joint mechano-receptors. The reflex response of muscles articulating a joint is facilitated by a low external SMS pressure intensity and inhibited by a high external SMS pressure intensity.

18 Claims, 6 Drawing Sheets

FIG. 1
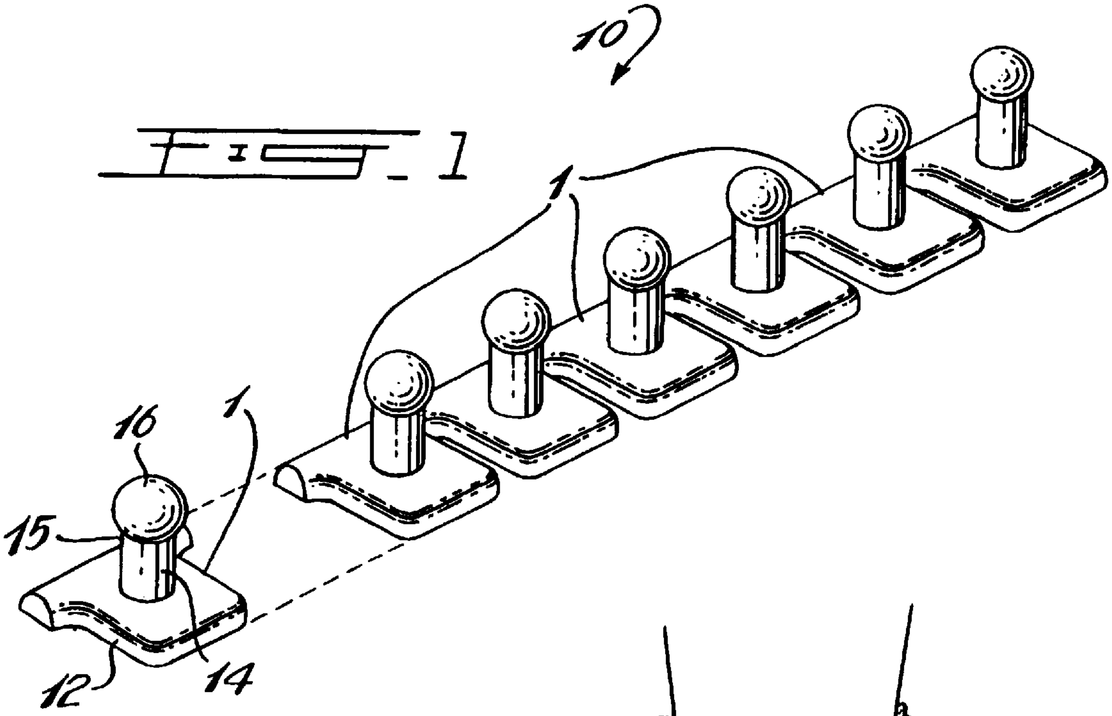
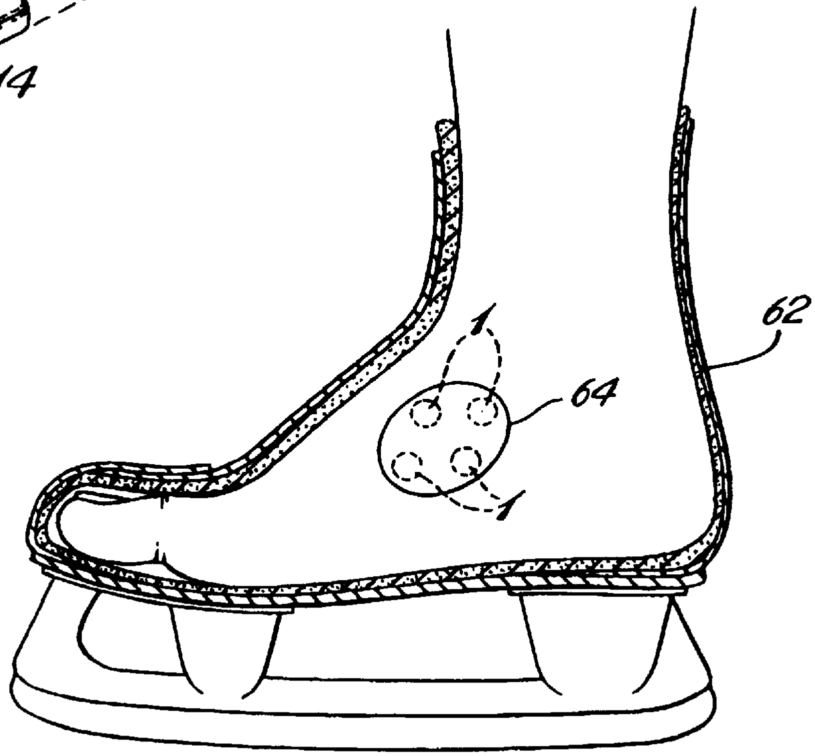
FIG. 2

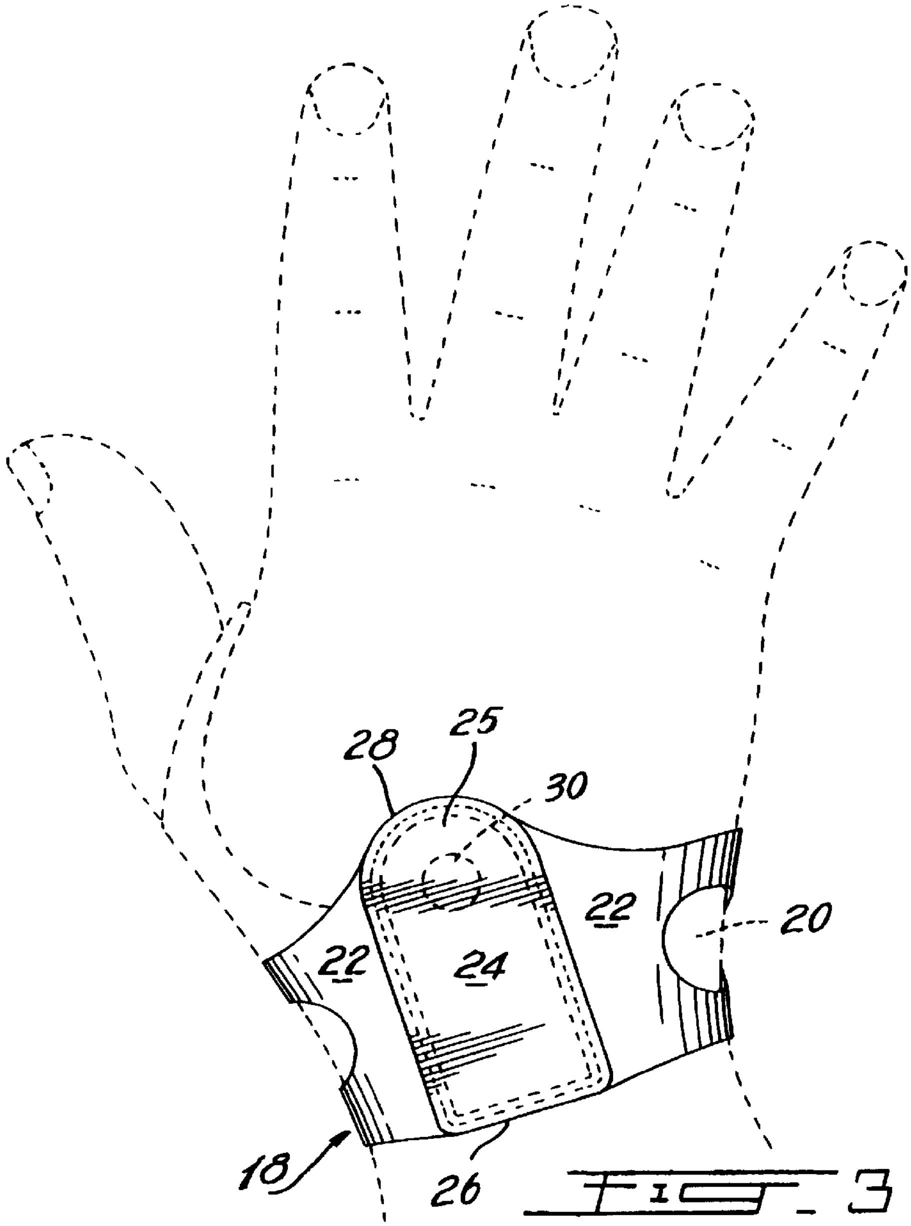
FIG. 3
FIG. 4
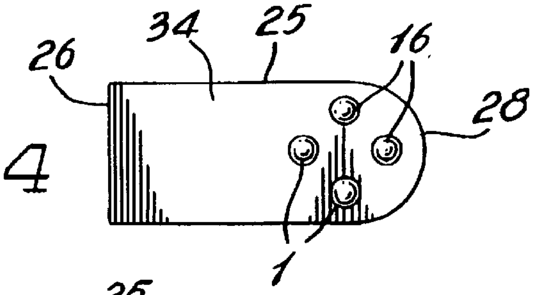
FIG. 4A
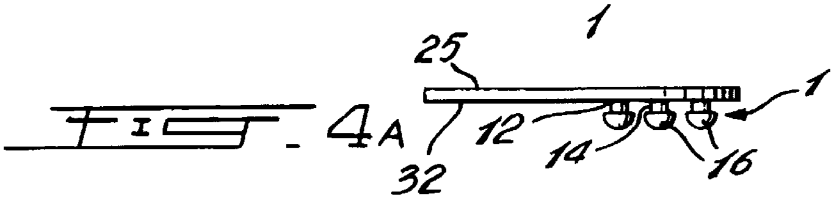

PREVENTION FACILITATOR SUPPORT FOR THE WRIST, ANKLE AND SACRO-LUMBAR JOINTS

FIELD OF THE INVENTION

Generally, the present invention relates to a device using specific mechanical stimulation (external pressure) to control the reflex response of a muscle or muscular group articulating a living body joint. More specifically, the present Invention relates to such a device for continuously applying an external pressure to, in particular but not exclusively, the wrist, ankle or lumbar spine joints during articulating movements of these joints to thereby continuously facilitate or inhibit the reflex response of their associated muscles.

BACKGROUND OF THE INVENTION

Often individuals having one or many joints or muscles which are over solicited suffer from repetition motion syndromes A method and a device using a specific mechanical stimulation (SMS) at an articulated body joint to facilitate or to inhibit the reflex response of the associated muscles, thus preventing these muscles from being over solicited or enabling them to relax is described in U.S. Pat. No. 5,769,810 granted to Brossard on Jun. 23, 1998.

The prior art teaches that the natural reflex mechanism of muscles associated with articulating joints such as the wrist, ankle and lumbar spine is guided by the respective mechano-receptors of these muscles. It was described that a light SMS pressure intensity (≤200 mmHg) stimulates only skin mechano-receptors (such as the Pacinian corpuscles) of the wrist ankle and lumbar spine joints, hence facilitating the reflex response of the muscles associated with these joints, improving the efficiency thereof On the contrary, a high SMS pressure intensity (≥400 mmHg) stimulates the above mentioned skin mechano-receptors and deeper joint mechano-receptors (such as Golgi tendons) of the wrist, ankle and lumbar spine joints to Inhibit the reflex response (reduction of the reflex response) of the respective muscles, thereby relaxing these muscles. Furthermore, it was observed that a medium pressure intensity (>200 mmHg but <400 mmHg) has substantially no effect. The information from the mechano-receptors is transmitted to many levels of the central nervous system. Mainly, the information from the mechano-receptors is transmitted to the spinal cord and brain. As the information is transmitted to the spinal cord, it influences the motor reflexes. Being transmitted to the brain it also influences central control of the joint movements.

U.S. Pat. No. 5,769,810 describes generally hemispherical pressure-applying protuberances for applyying either a low or high SMS pressure to specific external areas of the wrist, ankle and lumbar spine joints. These specific external areas correspond to the mechano-receptors, These pressure-applying members are mounted to support members adapted to be mounted to the wrist, ankle and lumbar spine joints.

The limitation with the prior art is that there are variations in distance between the body joint and the respective support member during certain articulating movements. These articulating movements further cause movements of the pressure-applying protuberance, causing variations in the SMS pressure intensity applied to the stimulated area(s). The disadvantages are that these variations sometimes fall within the middle pressure intensity (>200 mmHg but <400 mmHg) or that the protuberance Is no longer engaging the stimulated area, nullifying the effect of the prior art device.

OBJECTS OF THE INVENTION

The general object of the present invention is to obviate the above-mentioned disadvantages Another object of the invention is to provide a device capable of continuously applying specific mechanical stimulation (SMS) to an articulated body joint during articulating movements of this joint.

A further object of the present invention is to provide a pressure-applying device comprising a pressure-applying body that can be mounted or integrated to a variety of support members adapted to be mounted to the wrist, ankle and lumbar spine joints.

SUMMARY OF THE INVENTION

More particularly, in accordance with the present invention, there is provided a device for controlling the reflex response of a muscle or muscular group articulating a joint of a living body, the living body having mechano-receptors guiding a natural reflex mechanism of the muscle or muscular group. This device comprising:

a support member mounted to the joint of the living body;

a pressure-applying member mounted on the support member for applying pressure to an external area of the joint which corresponds to the mechano-receptors, submitting the mechano-receptors to a pressure intensity adequate to facilitate or inhibit the reflex response of the muscle or muscular group; and a resilient member interposed between the support member and the pressure-applying member. This resilient member is deformable to compensate for variations of a distance between the support member and the external area during articulation movements of the joint and thereby enable the pressure-applying member to continuously submit the mechano-receptors to the pressure intensity.

In accordance with preferred embodiments:

the resilient member comprises a platform and an arm extending therefrom, the arm has a free end carrying the pressure applying member and the platform, the arm and the pressure-applying member are made of a single piece of resilient material;

the resilient member comprises a receptacle including resilient material, and the pressure-applying member comprises an arm mounted in the receptacle, the resilient material being deformable to bias the arm away from the receptacle;

the receptacle is substantially resilient and the arm is substantially rigid and the receptacle and arm have respective mutually mating arm-receiving and receptacle-engaging portions for preventing the arm from being disassociated from the receptacle;

the resilient member comprises a receptacle with a hole therein, the pressure-applying member is mounted to a first end of an arm, the arm is slidably mounted in the hole of the receptacle for longitudinal movement therein, a spring carried by the arm, between the receptacle and the pressure-applying member, to spring-bias the arm and the pressure-applying member away from the receptacle, a stopper is carried by a second end of the arm and the stopper abuts against the receptacle to prevent the arm from being disassociated from the receptacle; and the pressure-applying member is a generally spherical-shaped protuberance.

In accordance with another preferred embodiment of the present invention:

the mechano receptors comprise skin mechano-receptors and the support and resilient members comprise means for applying the pressure-applying member to the external area to submit the mechano-receptors to a light pressure intensity ≤200 mmHg for stimulating only the skin mechano-receptors and thereby increasing the reflex response of the muscle or muscular group; and the mechano-receptors comprise deeper joint mechano-receptors including at least one Golgi tendon, and the support and resilient members comprising means for applying the pressure-applying member to the area to submit the mechano-receptors to a high pressure intensity ≥400 mmHg for stimulating the joint mechano-receptors and thereby inhibiting the reflex response of the muscle or muscular group.

When the joint of the living body is a wrist joint the support member may comprise a wrist band with the pressure-applying and resilient members mounted thereto to apply pressure to the area of the dorsal radiocarpal ligament. Preferably, the wrist band comprises a main body and a fastener portion. The main body has one side facing the external area of the dorsal radiocarpal ligament, and the pressure applying and resilient members are enclosed within the main body with the pressure-applying member directed towards the side of the main body facing the external area.

When the joint of the living body is an ankle joint, the support member may comprise an ankle band or footwear with the pressure-applying and resilient members mounted thereon or in the latter case integrated thereto to apply pressure to the external area of the calcaneofibular ligament, lateral talocalcaneal ligament, and interosseous talocalcaneal ligament. Preferably, the ankle band comprises a main body and a fastener portion. The main body having one side facing the area of the calcaneofibular ligament, lateral talocalcaneal ligament, and interosseous talocalcaneal ligament, and the pressure-applying and resilient members being enclosed within the main body with the pressure-applying member directed towards the side of the main body facing the external area.

When the joint of the living body is a lumbar spine, the support may comprise a pair of shorts formed with an insert-receiving pocket, and a generally flat pressure-applying insert mounted in the pocket of the shorts, the pressure-applying insert comprising a plurality of sets of pressure-applying members to apply pressure to the external area of the intraspinalis muscles, intraspinalis ligaments, intratransverse muscles, intratransverse ligaments, semispinalis muscles, semispinalis ligaments, sacrospinalis muscles, sacrospinalis ligaments, iliopsoas muscles, iliopsoas ligaments, piriformis muscles, and piriformis ligaments.

The objects, advantages and other features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 1 is a perspective view of a preferred embodiment of the pressure-applying assembly according to the present invention;

FIG. 2 Is a side sectional view of a human foot wearing an ice skate;

FIG. 3 is a top plan view of a human wrist and hand wearing an elastic wrist band;

FIGS. 4 and 4*a* are a bottom plan view and a side elevational view respectively of an insert forming part of the elastic wrist band of FIG. 3;

DESCRIPTION OF THE PREFERRED EMBODIMENTS

Figure 5:
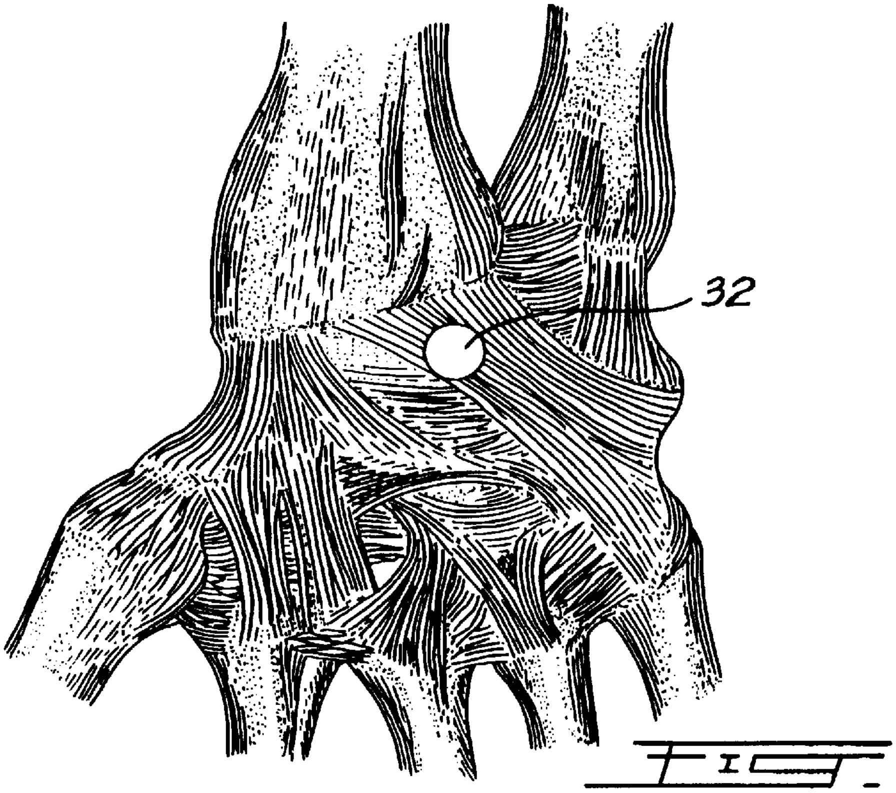
FIG. 5 is a schematic representation of the ligaments of the dorsal aspect of the left wrist.

FIG. 1 illustrates a preferred embodiment of a plurality of pressure-applying assemblies 1 according to the present invention. The assemblies 1 can be attached such as in a series 10 or in another type of attachment or sliced off from series 10 to be used alone or to be reassembled depending on the requirement of the intended application. Each assembly 1 comprises a resilient member in the form of a platform 12, an arm 14 extending from one side of the platform 12. The arm 14 carries on its top free end 15 a pressure-applying member 16 preferably being a generally spherical or hemispherical protuberance. Platform 12, arm 14 and protuberance 16 are preferably made of a one piece unit made from the same resilient material. Alternately, platform 12, arm 14 and protuberance 16 can be distinct pieces connected together for operative use with either platform 12 and arm 14 or platform 12 alone being made from resilient material.

Also, the complete series 10 of pressure apllying assemblies 1 can be made of a single piece of resilient material such as for example rubber or plastic foam material. Obviously, the use of other types of materials can be contemplated.

Figure 9:
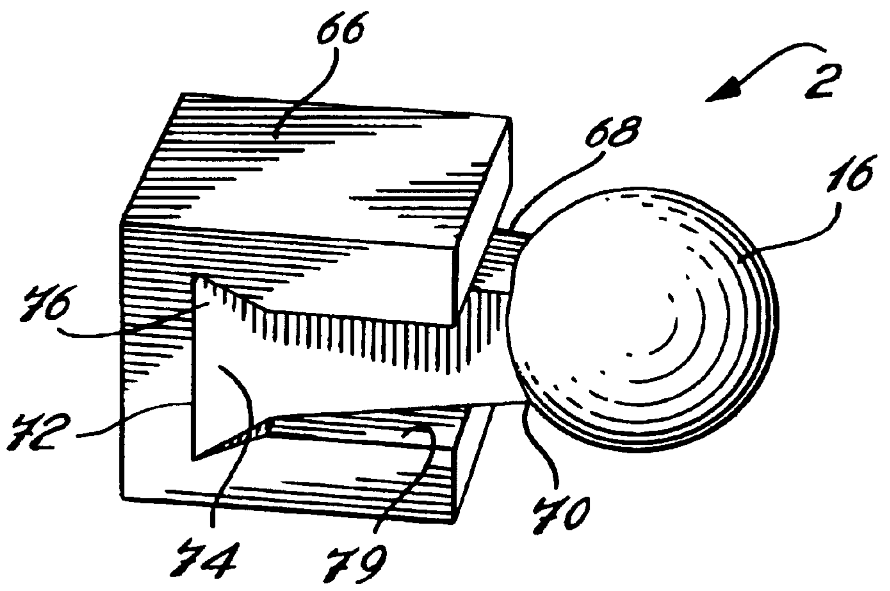
FIG. 9 is a perspective view of another preferred embodiment of the pressure-applying assembly according to the present invention.
Figure 10:
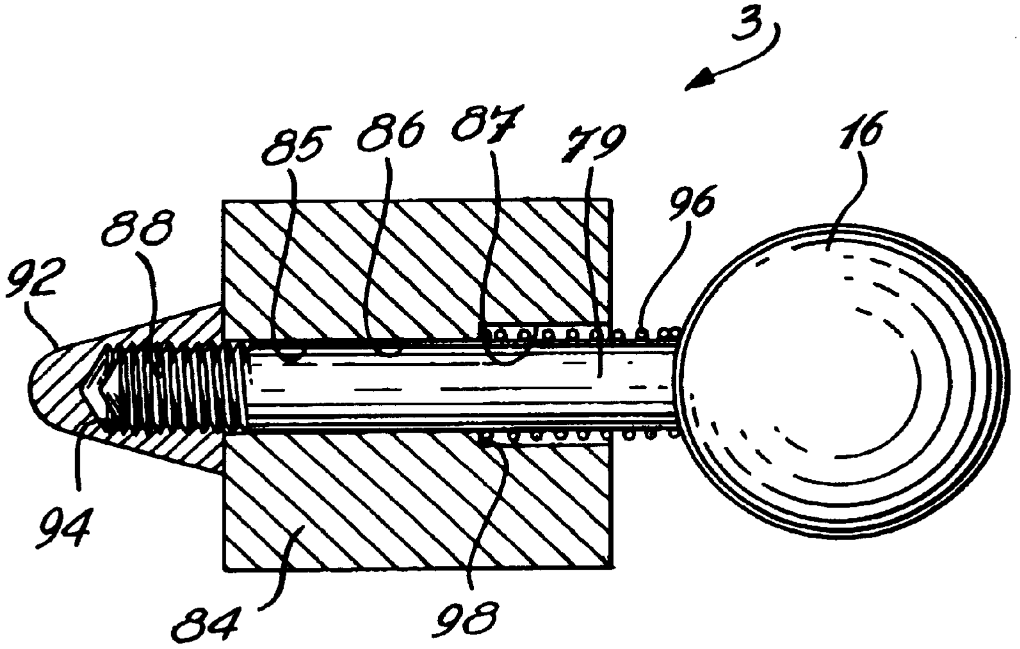
FIG. 10 is a lateral elevational cross sectional view of a further preferred embodiment of the pressure-applying assembly according to the present invention.

The pressure-applying assemblies 1 of FIG. 1 and variations thereof such as assemblies 2 and 3 of FIGS. 9 and 10 are utilized to apply a specific mechanical stimulation (SMS) to the external areas of an articulated joint such as the writ, ankle and lumbar spine joints of a living body, preferably a living human body, which correspond to the mechano-receptors of the muscle or muscular groups associated with this joint in the manner disclosed In U.S. Pat. No. 5,769,810. Hence, the pressure-applying assemblies of the present invention are adapted and constructed so as to either continuously apply a light intensity external SMS pressure (≤200 mmHg), which stimulates the skin mechano-receptors and facilitates the reflex response of the muscle or muscular groups, or a high intensity SMS pressure (≥400 mmHg), which stimulates the deeper joint mechano-receptors and inhibits the reflex response of the muscle or muscular group. Pressure-applying assemblies 1, 2 and 3 are mounted or integrated to a variety of support members such as, without limitation, various wrist and ankle bands, various casual and sports footwear, shorts and the like.

FIG. 3 shows a non-limiting example of a wrist band 18, made at least in part of substantially elastic material, for example the foamy elastic fabric material for which are made the dry and wet suits currently used in water sports. The wrist band 18 is placed around a user's wrist joint 20 and fastened thereon. For example, the wrist band 18 comprises two end sections 22 attached together by superposing strips of VELCRO™ loop material (not shown). The wrist band 18 is formed with a main body 24 including an additional layer of material such as fabric or leather secured to the material of the band 18 to define a pocket 23, between these two sewed layers of material. A flat and generally elongate insert 26 (FIG. 4*a*) inserted in pocket 23. The insert 25 has a rectangular end 28 and a generally semicircular end 28 to conform with the shape of the pocket 23 formed by the main body 24. The flat insert body 25 carries pressure-applying assemblies 1 in the region of the semicircular end 28.

The muscular composition of wrist 20 is shown in FIG. 5 revealing area 32 corresponding to the mechano-receptors of the dorsal radial carpal ligament. Insert 26 carries pressure-applying assemblies 1 on one side 34 (FIG. 4*a*), in region 30 of the main body 24 which is superposed to area 32. The pressure-applying membes 16 face the wrist joint 20 so as to apply an external SMS pressure on area 32. Platform 12 can be either attached to insert 25 by a glue substance or any other means apparent to one skilled in the art or be integrated into flat insert 26.

Figure 7:
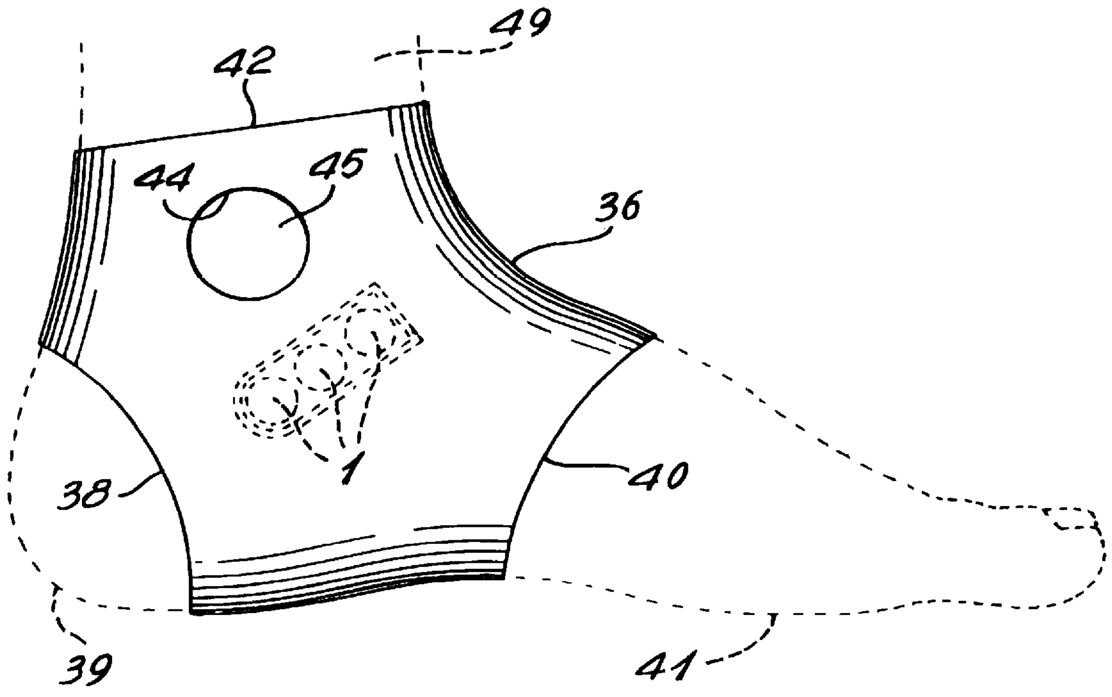
FIG. 7 is a side elevational view of a human ankle wearing a sock-like elastic ankle band.

A non-limiting example of an ankle band 36 is illustrated in FIG. 7. The elastic ankle band is formed with an opening 38 for the user's heel 30, an opening 40 for the user's foot 41, an opening 42 for the user's leg 43 and an opening 44 for each malleolus 45 of the user. The ankle band 36 may be made for example of the foamy substantially elastic fabric material of which are made the dry or wet suits currently used in water sports. In this example, the sock-like ankle band 36 is formed with a pocket 48 to receive an insert 48 carrying a group of pressure-applying assemblies 1. Pocket 48 may be formed by securing an additional layer of material such as fabric or leather to the material of the sock-like ankle band 36. Again, the pressure-applying members 16 face the ankle joint so as to apply the external SMS pressure.

Figure 6:
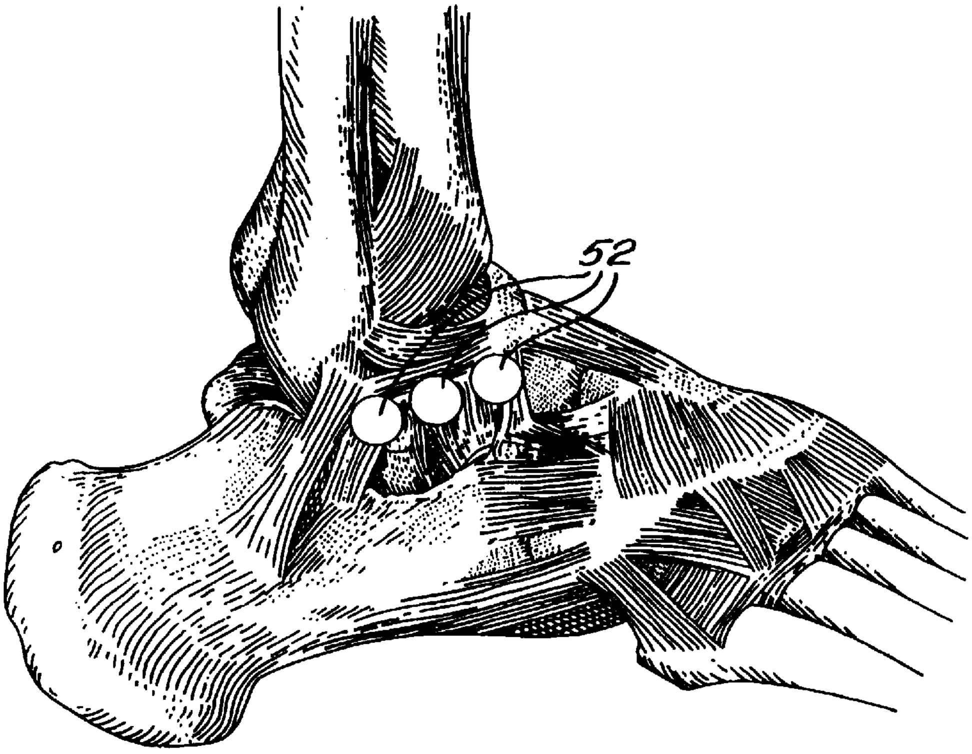
FIG. 6 is a schematic representation of the ligaments of a human ankle joint.

The muscular composition of the ankle joint 50 is illustrated in FIG. 6 which reveals areas 52 corresponding to the mechano-receptors of the calcaneofibular ligament, the lateral talocalcaneal ligament, and the interosseous talocalcaneal ligament. Again, like in the example of wrist band 18, the pressure-applying assemblies 1 are placed on the side of the insert 48 which faces the ankle 50 and in the regions of the insert 48 corresponding to areas 52.

It should be noted that inserts 25 and 48 may comprise a plurality of protuberances smaller than and replacing those Illustrated in FIG. 4*a*, it should be understood that such smaller protuberances would cover a larger surface than those illustrated herein.

Figure 8:
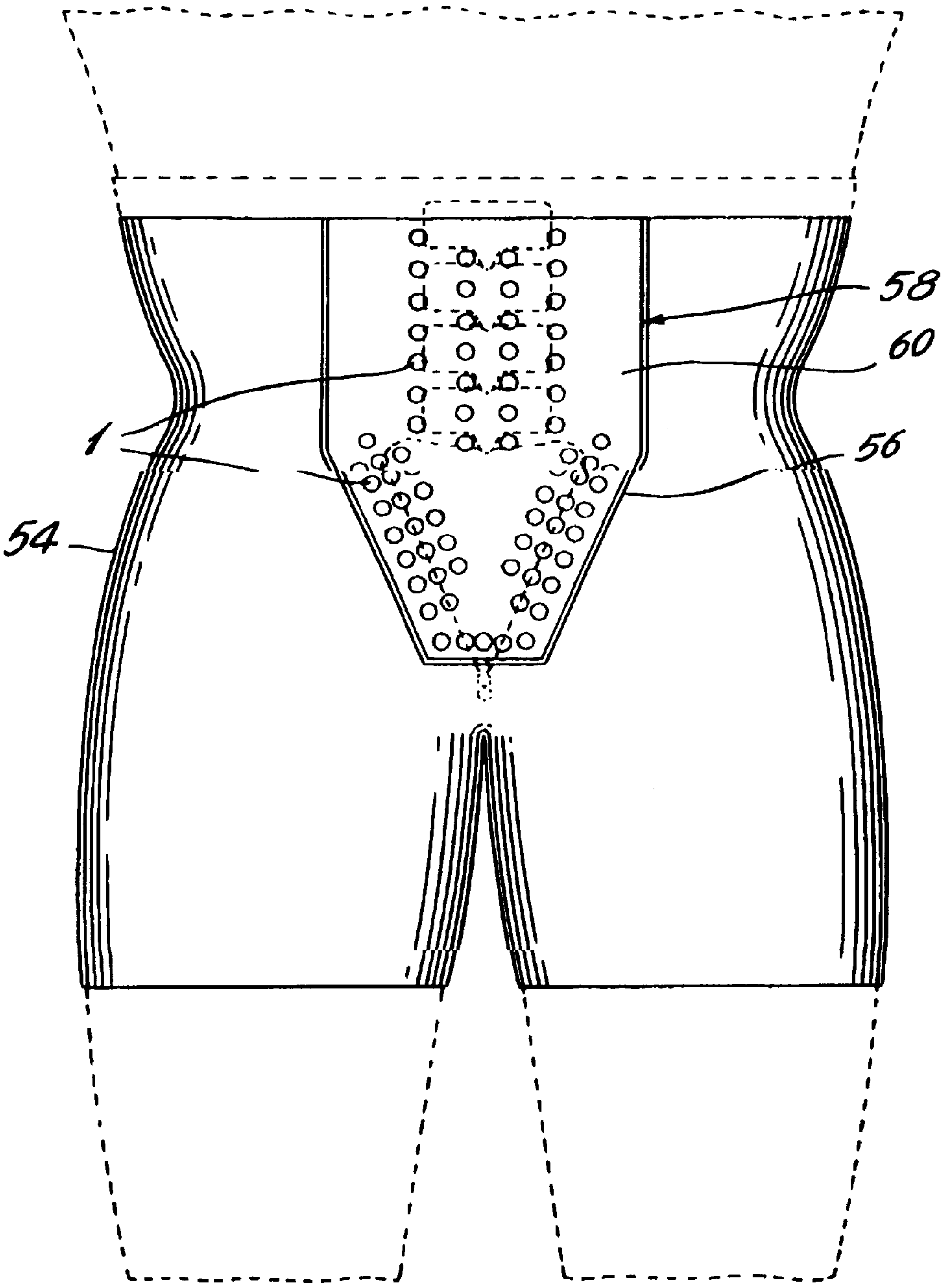
FIG. 8 is a rear elevational view of extensible cyclist shorts having a rear pocket to receive an insert comprising a flat body formed on one side with numerous pressure-applying assemblies.

As illustrated in FIG. 8, the same concept can be applied to the lumbar spine. In that particular case, extensible cyclist shorts 54 are provided with a rear pocket 56 to receive a flat insert 58. Pocket 56 is formed by sewing an additional inside layer of extensible fabric material to the extensible shorts 54.

The flat insert 58 comprises a flat body 60 on one side of which ax formed numerous pressure-applying assemblies 1 to apply a pressure (SMS) in the region of the intraspinalis muscles, intraspinalis ligaments, intratransverse muscles, intratransverse ligaments, semispinalis muscles, semispinalis ligaments, sacrospinalis muscles, sacrospinalis ligaments, iliopsoas muscles, iliopsoas ligaments, piriformis muscles, piriformis ligaments.

The pressure-applying assemblies 1 may also be mounted to casual or athletic footwear such as, without limitation, various sorts of running shoes, ski-boots, roller skates, roller blades or ice skates an example of which is illustrated in FIG. 2. In this example, pressure-applying assemblies 1 have been integrated to the skate 62 in region 64 which is superposed to the area of the ankle corresponding to the mechano-receptors to apply a pressure (SMS) thereto. The pressure-applying assemblies 1 can be mounted to an insert which in turn is enclosed within skate 62 or directly integrated to skate 62 in any suitable manner.

Other types of wrist and ankle bands, shorts and footwear and means of operatively connecting the pressure-applying assemblies 1, 2, and 3 (FIGS. 1, 9 and 10) to such support members in accordance with the present invention will become apparent to one skilled in the art.

With particular reference to FIGS. 1 and 4*a* the resilient portion of the pressure-applying assembly, platform 12 and arm 14, Is interposed between the pressure applying member and support member (such as wrist 18 and ankle 34 bands, shorts 54 and athletic footwear 62) so as to bias pressure-applying member 16 away from the support member and toward the external area of the body joint corresponding to the mechano-receptors of the muscle associated with that joint. Therefore, in all of the above-described embodiments, when the wrist, ankle or lumbar spine joint is articulated the distance between the support member and the stimulated external area (such as areas 32 and 52 of FIGS. 5 and 6 respectively), may vary and the resilient portion (platform 12 and arm 14) will compensate for that variation of distance by deforming to continuously apply the pressure-applying member 16 to the stimulated area, to thereby apply the SMS pressure during articulation movements of the joints. Furthermore, platform 12 and arm 14 are sufficiently flexible to allow the user to comfortably articulate a given joint without resistance during articulation movements while applying required SMS pressure intensity.

In another embodiment of the present invention illustrated in FIG. 9 the pressure-applying assembly 2 comprises a block-like receptacle 66 which receives an arm 68 carrying at a first end 70 a pressure-applying member 16 formed by a substantially spherical protuberance. The receptacle 66 is preferably made of substantially resilient material to form a resilient member. At least the inner back wall 72 of the receptacle 66 is made of substantially resilient material. Preferably, arm 68 is substantially rigid and forms a one piece unit with pressure-applying member 16. Arm 68 engages at its other free end 74 the resilient inner back wall 72 which is deformable such that it biases arm 68 and pressure-applying member 16 away from receptacle 66. The arm flares outwardly in the direction of the end 74 to define a receptacle-engaging portion 76 mating with a complementary arm-receiving portion 78 of receptacle 86. This arm-receiving portion 78 comprises a bottom formed by the inner back wall 72. The receptacle-engaging portion and arm receiving portion 78 prevents the arm 68 from disengaging the receptacle 66.

Again the same concept applies in this particular embodiment. The resilient wall 72 deforms when the body joint is articulated to compensate for the variation of distance between the stimulated external area of the body joint and the support member. In this manner, a SMS pressure is continuously applied to the stimulated external area.

In a further preferred embodiment of the present invention illustrated in FIG. 10 the pressure-applying assembly 3 comprises an arm 79 carrying a pressure-applying member 16 at one end 80. The arm 79 is slidably mounted in an arm-receiving hole 86 of a receptacle 84. The Arm 79 has a threaded second end 88 protruding on the side 90 of the receptacle 84 opposite to pressure-applying member 16. A conical stopper 92 has an internally threaded portion 94 screwed on second end 88. The conical stopper 92 abuts the back face 90 of the receptacle 84 to prevent the arm 79 and pressure-applying member to disengage that receptacle 84, Male 86 has smaller and larger diameter portions 85 and 87 forming a shoulder 98. Larger diameter portion 87 has a diameter sufficiently wide to receive both the arm 79 and a spring 96, smaller portion 85 has a diameter wide enough to receive arm 79 only. Spring 98 extends along the length of arm 79 and is compressed between shoulder 98 and pressure-applying member 16. Accordingly, spring 96 rests at one and on the shoulder 98 and at the other end on the pressure-applying member 16. That spring 96 defines a resilient member and biases pressure-applying member 18 away from receptacle 84.

When assembly 3 is mounted to a support member, itself mounted to a body joint, articulation of that joint will cause variations of distance between the support and the external area of the joint to be stimulated. Spring 96 will deform to compensate for this variation in distance hence, member 16 will continuously apply the required SMS pressure intensity during articulation movements.

Although the present invention has been described hereinabove by way of preferred embodiments thereof, it can be modified, without departing from the spirit and nature of the subject invention as defined in the appended claims.

What is claimed is:

1. A device for controlling the reflex response of a muscle or muscular group articulating a joint of a living body, the living body having mechano-receptors guiding a natural reflex mechanism of the muscle or muscular group, said device comprising:

- a support member adapted to be mounted to the joint of the living body;
- a pressure-applying member mounted on said support member, and applying pressure to an external area of the joint which corresponds to the mechano-receptors thereby submitting the mechano-receptors to a pressure intensity adequate to facilitate or inhibit the reflex response of the muscle or muscular group; and
- a resilient assembly comprising an arm extending between said support member and said pressure-applying member, wherein:
  - said arm has a free end carrying said pressure applying member; and
  - said resilient assembly deforms during articulation movements of the joint to enable said pressure-applying member to continuously submit the mechano-receptors to said pressure intensity.

2. A device as defined in claim 1 wherein said resilient assembly further comprises a platform, said arm extending from said platform.

3. A device as defined in claim 2 wherein said platform, said arm and said pressure-applying member are a single piece of resilient material.

4. A device as defined in claim 1 wherein said pressure-applying member is a generally spherical-shaped protuberance.

5. A device as defined in claim 1, wherein the mechano-receptors comprise skin mechano-receptors, and wherein said support member and resilient assembly comprise means for applying said pressure-applying member to the external area of the joint to submit mechano-receptors to a light pressure intensity for stimulating only the skin mechano-receptors and thereby increasing the reflex response of the muscle or muscular group.

6. A device as defined in claim 5, wherein said light pressure intensity is $\lesssim$200 mmHg.

7. A device as defined in claim 6, wherein said wrist band comprises a main body and a fastener portion, said main body having one side facing the external area of the dorsal radiocarpal ligament, and wherein said pressure-applying member and resilient assembly are enclosed within said main body with said pressure-applying member directed towards said one side of the main body.

8. A device as defined in claim 1, wherein the mechano-receptors comprise deeper joint mechano-receptors, and wherein said support member and resilient assembly comprise means for applying said pressure-applying member to the external area to submit the mechano-receptors to a high pressure intensity for stimulating the joint mechano-receptors and thereby inhibiting the reflex response of the muscle or muscular group.

9. A device as defined in claim 8, wherein the deeper joint mechano-receptors comprise at least one Golgi tendon of the muscle or muscular group, and wherein said high pressure intensity is 400 mmHg.

10. A device as defined in claim 1, wherein the joint of the living body is a wrist joint, and wherein said support member comprises a wrist band with said pressure-applying member and resilient assembly mounted thereto to apply pressure to the area of the dorsal radiocarpal ligament.

11. A device as defined in claim 1, wherein the joint of the living body is an ankle joint, and wherein said support member is an ankle band with said pressure-applying member and resilient assembly mounted thereto to apply pressure to the external area of the calcaneofibular ligament, lateral talocalcaneal ligament, and interosseous talocalcaneal ligament.

12. A device as defined in claim 11, wherein said ankle band comprises a main body and a fastener portion, said main body having one side facing the area of the calcaneofibular ligament, lateral talocalcaneal ligament, and interosseous talocalcaneal ligament, and wherein said pressure-applying member and resilient assembly are enclosed within said main body with said pressure-applying member directed towards said one side of the main body.

13. A device as defined in claim 1, wherein the joint of the living body comprises a lumbar spine, and wherein said support member comprises shorts formed with an insert-receiving pocket, and a generally flat pressure-applying insert mounted in the pocket of the shorts, said pressure-applying insert comprising a plurality of pressure-applying assemblies, said pressure-applying assemblies each comprising said resilient assembly and said pressure-applying member to apply pressure to the external area of the intraspinalis muscles, intraspinalis ligaments, intratransverse muscles, intratransverse ligaments, semispinalis muscles, semispinalis ligaments, sacrospinalis muscles, sacrospinalis ligaments, iliopsoas muscles, iliopsoas ligaments, piriformis muscles, and piriformis ligaments.

14. A device as defined in claim 1 wherein the joint of the living body comprises an ankle joint and wherein said support member comprises footwear with said pressure-applying member and resilient assembly integrated thereto to apply pressure to the external area of the joint which corresponds to the mechano-receptors.

15. A device for controlling the reflex response of a muscle or muscular group articulating a joint of a living body, the living body having mechano-receptors guiding a natural reflex mechanism of the muscle or muscular group, said device comprising:

- a support member adapted to be mounted to the joint of the living body;

a pressure-applying member mounted on said support member, and applying pressure to an external area of the joint which corresponds to the mechano-receptors thereby submitting the mechano-receptors to a pressure intensity adequate to facilitate or inhibit the reflex response of the muscle or muscular group; and a resilient assembly comprising an arm having a free end carrying the pressure-applying member, and a receptacle including resilient material; wherein:

said arm extends between the pressure-applying member and the receptacle and comprises a second end mounted in said receptacle; and said resilient material deforms during articulation of the joint to bias said arm away from said receptacle to compensate for variations of a distance between said support member and the external area of the joint during articulation movements of the joint and thereby enable said pressure-applying member to continuously submit the mechano-receptors to said pressure intensity.

16. A device as defined in claim 15 wherein said receptacle is substantially resilient and said arm is substantially rigid and wherein said arm and receptacle have respective mutually mating receptacle-engaging and arm-receiving portions for preventing said arm from being disassociated from said receptacle.

17. A device for controlling the reflex response of a muscle or muscular group articulating a joint of a living body, the living body having mechano-receptors guiding a natural reflex mechanism of the muscle or muscular group, said device comprising:

a support member mounted to the joint of the living body;

a pressure-applying member mounted on said support member, and applying pressure to an external area of the joint which corresponds to the mechano-receptors thereby submitting the mechano-receptors to a pressure intensity adequate to facilitate or inhibit the reflex response of the muscle or muscular group; and a resilient assembly comprising a receptacle with a hole therein, an arm having a first end on which said pressure-applying member is mounted, said arm being slidably mounted in the hole of said receptacle for longitudinal movement, and a spring carried by said arm, between said receptacle and said pressure-applying member, to spring-bias said arm and said pressure-applying member during articulation of the joint away from said receptacle to compensate for variations of a distance between said support member and the external area of the joint during articulation movements of said joint and thereby enable said pressure-applying member to continuously submit the mechano-receptors to said pressure intensity.

18. A device as defined in claim 17 further comprising a stopper carried by a second free end of said arm, said stopper abutting against said receptacle to prevent said arm from being disassociated from said receptacle.

* * * * *